United States Patent [19]

Lagrange et al.

[11] Patent Number: 5,583,234

[45] Date of Patent: Dec. 10, 1996

[54] INDOLINE-BASED PRODUCTS, PROCESSES FOR PREPARING THEM AND THEIR USE IN COSMETICS

[75] Inventors: Alain Lagrange, Chatou; Hervé Andrean, Paris; Alex Junino, Livry-Gargan, all of France

[73] Assignee: L'Oreal, Paris, France

[21] Appl. No.: 119,072

[22] PCT Filed: Jan. 13, 1993

[86] PCT No.: PCT/FR93/00030

§ 371 Date: Dec. 29, 1993

§ 102(e) Date: Dec. 29, 1993

[87] PCT Pub. No.: WO93/13744

PCT Pub. Date: Jul. 22, 1993

[30] Foreign Application Priority Data

Jan. 16, 1992 [FR] France ..................... 92 00416

[51] Int. Cl.⁶ .......................... A61K 7/13; C07D 209/10
[52] U.S. Cl. .................... 548/455; 548/460; 548/490; 548/491; 424/59; 424/61; 424/62; 424/63; 424/401
[58] Field of Search ................... 548/455, 460, 548/490, 491; 424/401, 59, 61, 62, 63

[56] References Cited

U.S. PATENT DOCUMENTS 4,013,404 3/1977 Parent et al. .................. 8/11

FOREIGN PATENT DOCUMENTS

| 0379409 | 7/1990 | European Pat. Off. . |
|---|---|---|
| 0441689 | 8/1991 | European Pat. Off. . |
| 0462857 | 12/1991 | European Pat. Off. . |
| 2207153 | 1/1989 | United Kingdom . |
| WO90/01919 | 3/1990 | WIPO . |
| WO90/10430 | 9/1990 | WIPO . |
| WO91/17739 | 11/1991 | WIPO . |

*Primary Examiner*—Jacqueline Haley
*Attorney, Agent, or Firm*—Jacobson, Price, Holman & Stern, PLLC

[57] ABSTRACT

An indoline product obtained by oxidizing at least one compound of formula (I),

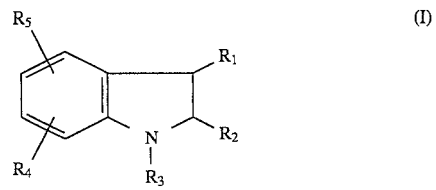

wherein $R_1$ and $R_3$ independently represent a hydrogen atom or a $C_{1-4}$ alkyl grouping; $R_2$ represents a hydrogen atom, a $C_{1-4}$ alkyl grouping, a carboxyl grouping or $C_{1-4}$ alkoxycarbonyl; $R_4$ is a hydrogen atom, a $C_{1-4}$ alkyl grouping, hydroxyl, $C_{1-4}$ alkoxy, $C_{1-10}$ amino or alkylamino, or halogen; $R_5$ is a hydrogen atom, a hydroxyl grouping, $C_{1-4}$ alkoxy or amino; with the proviso that at least one of the radicals $R_4$ or $R_5$ is a hydroxyl, alkoxy or amino grouping, and that when $R_5$ is an amino grouping, $R_4$ is not an alkylamino radical; $R_4$ and $R_5$ may also form a $C_{1-2}$ alkylenedioxy ring and are in positions 5 and 6; and corresponding salts thereof. Said product may be used in cosmetics as make-up for the hair, eyebrows, eyelashes, nails, etc., and/or skin.

17 Claims, No Drawings

INDOLINE-BASED PRODUCTS, PROCESSES FOR PREPARING THEM AND THEIR USE IN COSMETICS

This application is a National Stage application of PCT/FR93/00030 filed 13 Jan. 1993 and published as WO 93/13744 on 22 Jul. 1993.

The present invention relates to indoline-based products, to processes for preparing them, to their use in cosmetics and to cosmetic compositions employing them.

The use of colored pigments is of very great importance in the cosmetic field, in particular in makeup products intended for making up the exoskeleton and/or the skin.

Inorganic pigments or pigments derived from synthetic direct dyes, or from pure carbon in the case of black pigments, are generally used. These different products present, depending on the application, problems of use, and are not always problem-free from the standpoint of compatibility and toxicology.

The Applicant has discovered new products which can be used as pigments, especially in cosmetics, which are indoline-based products that are especially advantageous in respect of the colorations which they make it possible to obtain, as well as in their cosmetic use.

The products according to the invention are obtained by an oxidative polymerization process employing at least one indoline.

By analogy and for simplification, the term "indoline-based product" or "indoline-based polymer" will be used to denote the product obtained by oxidative polymerization of different compounds containing at least one indoline.

The subject of the present invention is hence new indoline-based products as defined below.

Another subject of the invention consists of the process for preparing these products.

The subject of the invention is also the cosmetic application of these indoline-based products, in particular the products for making up the skin and/or the exoskeleton and for protecting the human epidermis against UV radiation.

Other subjects of the invention will become apparent on reading the description and the examples which follow.

The indoline-based products according to the invention result from the oxidative polymerization of at least one indoline compound corresponding to the formula:

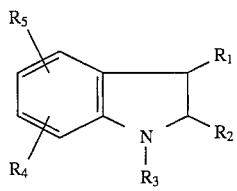

(I)

in which:

$R_1$ and $R_3$ represent, independently of one another, a hydrogen atom or a $C_1-C_4$ alkyl group;

$R_2$ represents a hydrogen atom, a $C_1-C_4$ alkyl group or a carboxyl or $(C_1-C_4$ alkoxy)carbonyl group;

$R_4$ denotes a hydrogen atom or a $C_1-C_4$ alkyl, hydroxyl, $(C_1-C_4$ alkoxy), amino or $C_1-C_{10}$ alkylamino or halogen group;

$R_5$ denotes a hydrogen atom or a hydroxyl, $C_1-C_4$ alkoxy or amino group;

on condition that at least one of the radicals $R_4$ or $R_5$ denotes a hydroxyl, alkoxy or amino group; and with the proviso that when $R_5$ denotes an amino group, $R_4$ cannot denote an alkylamino radical;

$R_4$ and $R_5$ can also form a $C_1-C_2$ alkylenedioxy ring, and are at positions 5 and 6;

as well as the corresponding salts.

Among the compounds corresponding to the formula (I), the preferred compounds used according to the invention are chosen from 5,6-dihydroxyindoline, 6-hydroxyindoline, 5,6-methylenedioxyindoline, 7-methoxy-6-hydroxyindoline, 6,7-dihydroxyindoline, 5-hydroxy-4-methoxyindoline, 4,5-dihydroxyindoline, 5-methoxy-6-hydroxyindoline, 4-hydroxy-5-methoxyindoline, 5-hydroxy-6-methoxyindoline, 4,7-dihydroxyindoline, 6-aminoindoline, N-ethyl-4-hydroxyindoline, 1-ethyl-6-amino-indoline, 5,6-diaminoindoline, 1-methyl-6-aminoindoline, 2-methyl-6-aminoindoline, 3-methyl-6-aminoindoline, 2-methyl-5,6-diaminoindoline, 5-chloro-7-aminoindoline, 3-methyl-5,7-diaminoindoline, 5,7-diaminoindoline, 2-methyl-5,7-diaminoindoline, 7-aminoindoline, 2-methyl-7-aminoindoline, 4-aminoindoline, 4-amino-6-chloroindoline, 4-amino-6-iodoindoline, 4-amino-5-bromoindoline, 4-amino-5-hydroxyindoline, 4-amino-7-hydroxyindoline, 4-amino-5-methoxyindoline, 4-amino-7-methoxyindoline, 5-aminoindoline, 2,3-dimethyl-5-aminoindoline, 1-methyl-5-aminoindoline, 2-methyl-5-aminoindoline, 5-[N-(1-methylhexyl)amino]indoline, 5,6-dimethoxyindoline and 5,6-dihydroxy-2-carboxyindoline.

In the compounds of formula (I), the $C_1-C_4$ alkyl radicals preferably denote methyl, ethyl, propyl, isopropyl, butyl, isobutyl. For the $C_1-C_{10}$ alkyl radicals, the $C_1-C_{10}$ alkyl radical preferably denotes methyl, ethyl, propyl, isopropyl, butyl, isobutyl, 1-methylhexyl, 1-methylheptyl, 1-methyloctyl; the alkoxy radicals preferably denote methoxy, ethoxy, propoxy and butyoxy; halogen denotes bromine, chlorine or iodine.

The salts are cosmetically acceptable salts, especially hydrochlorides, hydrobromides, sulfates, methanesulfonates. The hydrobromides of the above compounds are especially preferred.

The indoline-based products according to the invention may be obtained by cooxidation of at least one indoline corresponding to the formula (I) above with at least one indole derivative chosen from the mono- and dihydroxyindoles or the aminoindoles described, more especially, in Patent EP-A-239,826 and Patent Applications EP-A-425,345 and GB-A-2,224,754.

The indole derivatives are chosen, more especially, from the compounds of formula:

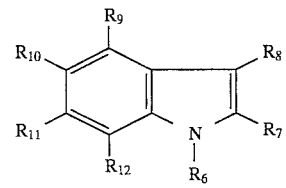

(II)

in which:

$R_6$ and $R_8$ denote, independently of one another, a hydrogen atom or a $C_1-C_4$ alkyl group;

$R_7$ represents a hydrogen atom, a $C_1-C_4$ alkyl group, a carboxyl group or a $(C_1-C_4$ alkoxy)carbonyl group;

$R_9$ and $R_{12}$ denote, independently of one another, a hydrogen atom, a hydroxyl group or a $C_1-C_4$ alkyl, amino, $(C_1-C_4$ alkoxy), $(C_2-C_4$ acyl)oxy or $(C_2-C_4$ acyl) amino group;

$R_{10}$ denotes hydrogen or a hydroxyl, $(C_1-C_4$ alkoxy), $(C_1-C_4$ alkyl), halogen, amino, $(C_2-C_{14}$ acyl)oxy, $(C_2-C_4$ acyl)amino or trimethylsilyloxy group;

$R_{11}$ denotes hydrogen or a hydroxyl, $(C_1-C_4$ alkoxy), amino, $(C_2-C_4$ acyl) oxy, $(C_2-C_4$ acyl)amino, trimethylsilyloxy or hydroxy($C_2-C_4$ alkyl)amino group;

$R_{10}$ and $R_{11}$, together with the carbon atoms to which they are attached, can form a methylenedioxy ring optionally substituted with a $C_1$–$C_4$ alkyl or $C_1$–$C_4$ alkoxy group or a carbonyldioxy ring;

at least one of the groups $R_9$ to $R_{12}$ represents a group OZ or NHR, not more than one of the groups $R_9$ to $R_{12}$ denoting NHR;

and not more than two of the groups $R_9$ to $R_{12}$ denote OZ, in the case where Z denotes hydrogen, these groups are at positions 5 and 6;

and at least one of the groups $R_9$ to $R_{12}$ represents hydrogen, in the case where only one of these groups denotes hydrogen, only one group from among $R_9$ to $R_{12}$ then denotes NHR or OZ and the other groups denote $C_1$–$C_4$ alkyl; R in NHR denoting a hydrogen atom or a $C_2$–$C_4$ acyl or $C_2$–$C_4$ hydroxyalkyl group, and Z in OZ denoting a hydrogen atom or a $C_2$–$C_{14}$ acyl, $C_1$–$C_4$ alkyl or trimethylsilyl group; and the corresponding salts.

The indole compounds of formula (II) are chosen especially from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-[N-(β-hydroxyethyl)amino]indole, 4-aminoindole, 5-aminoindole, 6-aminoindole, 7-aminoindole, N-methyl-6-(β-hydroxyethylamino)indole, 6-amino-2,3-dimethylindole, 6-amino-2,3,4,5-tetra-methylindole, 6-amino-2,3,4-trimethylindole, 6-amino-2,3,5-trimethylindole, 6-amino-2,3,6-trimethylindole, 5,6-diacetoxyindole, 5-methoxy-acetoxyindole and 5,6-dimethoxyindole.

5,6-Dihydroxyindole, 6-hydroxyindole, 3-methyl-5,6-dihydroxyindole, 2-methyl-5,6-dihydroxyindole, 1-methyl-5,6-dihydroxyindole and 2-carboxy-5,6-dihydroxyindole, used alone or mixed, are preferred.

When the indoline-based products according to the invention are prepared by cooxidation, it is possible to use up to 50 mol % of indole derivative relative to the total number of moles of derivatives to be oxidized.

The indoline-based products according to the invention may be prepared according to various processes of oxidative polymerization.

According to a first type of process, a simple oxidation in the air is carried out. In this case, no oxidizing agent other than aerial oxygen is used, and it is preferable to work at an alkaline pH in a water or water/solvent medium.

Oxidation in the air may also be performed in the presence of an alkaline agent and/or of a metal-based oxidation catalyst such as cuprio ion.

According to a second type of process, the preparation of the indoline-based products according to the invention may be performed in the presence of an oxidizing agent such as hydrogen peroxide, peracids and persalts.

Among peracids and persalts, periodic acid and its water-soluble salts, permanganates and dichromates such as those of sodium or potassium, ammonium persulfate and organic peracids may be mentioned.

The preferred periodic acid salt is sodium periodate.

Other oxidizing agents are chosen from alkali metal chlorites, silver oxide, ferric chloride, lead oxide, sodium nitrite; and rare-earth salts such as, in particular, cerium salts.

It is also possible to use organic oxidizing agents chosen from ortho- and para-benzoquinones, ortho- and para-benzoquinone monoimines and diimines, 1,2- and 1,4-naphthoquinones and 1,2- and 1,4-naphthoquinone mono- or diimines.

Lastly, the oxidation may be performed by the use of iodide such as an alkali metal or alkaline earth metal or ammonium iodide in the presence of hydrogen peroxide.

These oxidizing agents may be activated, where appropriate, with a pH-modifying agent.

The oxidation is generally carried out within a temperature range extending from room temperature to 100° C., with a preference for temperatures of between 20° and 80° C.

It is also possible to carry out the formation of the indoline-based products according to the invention by enzymatic oxidation. This oxidation is performed in an oxidizing medium and with an enzyme having oxidizing or peroxidizing activity, such as enzymes chosen from horseradish peroxidase, chloroperoxidase, milk peroxidase and cytochrome C peroxidase, as well as products having a similar activity, that of the peroxidizing enzymes, such as hemoglobin, methemoglobin, myoglobin and metmyoglobin. This enzymatic oxidation may also be performed in the presence of tyrosinase with aerial oxygen.

For the products intended for cosmetic application, it is preferable to use hydrogen peroxide, periodic acid and its salts, potassium permanganate, sodium hypochlorite, ammonium persulfate, sodium nitrite and the iodide/hydrogen peroxide system as oxidizing agents.

When an iodide is used in the presence of hydrogen peroxide, the preferred compound is sodium or potassium iodide at a weight concentration of between 1 and 6% relative to the weight of the reaction medium.

The order of addition of the compounds participating in the preparation of the indoline-based product, according to the invention, is of little importance provided that the oxidizing agent is incorporated last when the latter is used without a pH-modifying agent and, in the case of the iodide/hydrogen peroxide oxidizing system, either hydrogen peroxide or the iodide is introduced last.

In the case where a pH-modifying agent is used to activate the oxidizing agent, it is preferable to add either the oxidizing agent or the pH-modifying agent last.

The pH-modifying agents are acidifying or alkalinizing agents customarily used in cosmetics.

Before the addition of the oxidizing agent, the derivative to be oxidized is placed in aqueous solution or in a water/solvent medium with a proportion of solvent of between 0.5 and 95% or in a pure solvent medium.

The solvents are chosen from $C_1$–$C_4$ lower alcohols such as ethyl alcohol, propyl or isopropyl alcohol and tert-butyl alcohol, alkylene glycols such as ethylene glycol and propylene glycol, alkylene glycol alkyl ethers such as ethylene glycol monomethyl, monoethyl and monobutyl ethers and propylene glycol and dipropylene glycol monomethyl ethers, and methyl lactate.

These solvents must, moreover, be able to solubilize the indoline compound and, where appropriate, the indole derivative employed in order to form the indoline-based product.

The preferred solvent is ethanol, and the preferred oxidation medium is aqueous-alcoholic with an ethanol content of between 1 and 15%.

In the process according to the invention, the derivatives to be oxidized generally represent from 0.1 to 30%, and preferably from 1 to 20%, by weight of the total weight of the reaction medium.

The contact time between the derivatives to be oxidized and the oxidizing reagents can vary from a few minutes to a few days depending on the process.

The preferred alkaline agents are sodium hydroxide, alkali metal carbonates or ammonia solution. When they are used, their concentration in the oxidation medium is between $5 \times 10^{-4}$ and 10% by weight.

To prepare the indoline-based products according to the invention, it is preferable to use the process of oxidation with hydrogen peroxide in the presence of ammonia solution.

When the oxidation process is complete, the colored indoline-based product thereby formed is isolated by filtration, centrifugation or lyophilization. To remove the traces of derivatives to be oxidized which have not reacted, the product is rinsed copiously with water before or after filtration or centrifugation.

In the case where the indoline-based product according to the invention is prepared by simple oxidation in the air, it is preferable to isolate the indoline-based product by lyophilization.

In order to obtain a homogeneous product having a sufficiently fine particle size, it is thereafter possible to treat the product obtained by traditional grinding systems using the dry or wet method. It is also possible to use a micronization process.

The particle size of the final indoline-based product must be such that the average particle diameter is less than 50 microns, and preferably less than 20 microns. Likewise, 90% of the particles have a diameter which is generally less than 100 microns and preferably less than 50 microns.

The indoline-based products according to the invention are essentially polymers which are generally insoluble in the cosmetic media customarily used. These indoline-based products can, however, be dissolved in particular solvent media, for example using a medium whose pH is high.

The indoline-based products according to the invention, according to a subject of the invention, may be used in cosmetics, in particular in all products for the treatment or care of the skin and/or the exoskeleton. The term "exoskeleton" is used to denote the hair on the head and body, eyelashes, eyebrows and nails.

The indoline-based products according to the invention, in their cosmetic application, are used in cosmetic compositions in a cosmetically acceptable medium, at a concentration preferably of between 0.1 and 35% by weight, and especially between 0.5 and 20% by weight, relative to the total weight of the composition.

These compositions may be used as makeup products, in particular for the eyelashes, eyebrows, skin and nails, for instance in the form of eyeshadows, blushers, lining products also known as eyeliners, mascaras for the eyelashes and eyebrows and nail varnishes, and as dyeing compositions for hair, in particular for carrying out a temporary dyeing of the hair or makeup.

These compositions may also be used for protection of the human epidermis against UV radiation.

The compositions can take the form of a lotion, thickened lotion, gel, cream, milk, powder or stick, and can optionally be packaged as an aerosol and take the form of a foam or spray.

When the compositions are used for making up the skin, eyelashes and eyebrows, they can, in particular, take anhydrous or aqueous pasty or solid form, for example oil-in-water or water-in-oil emulsions or alternatively suspensions.

These compositions have the advantage of being especially stable and of affording complete safety.

When the compositions are used for protection of the human epidermis against UV radiation, they constitute so-called "sun" compositions, and they can take the form of suspensions or dispersions in solvents or fats, or alternatively the form of emulsions such as creams and milks, pomades, gels, solid sticks or aerosol foams.

When they are used in the form of emulsions, they can contain, in addition, surfactants which are well known in the prior art, such as anionic, nonionic, cationic or amphoteric surfactants.

The makeup compositions and the sun compositions can also contain fats, organic solvents, silicones, thickeners, demulcents, sunscreen agents, antifoams, hydrating agents, perfumes, preservatives, antioxidants, fillers, sequestering agents, treatment agents such as anionic, cationic, nonionic or amphoteric polymers or mixtures thereof, propellants and alkaninizing or acidifying agents.

The fats can consist of an oil or a wax or a mixture thereof, fatty acids, fatty alcohols, petroleum jelly, paraffin, lanolin, hydrogenated lanolin or acetylated lanolin.

The oils are chosen from animal, vegetable, mineral or synthetic oils, and in particular hydrogenated palm oil, hydrogenated castor oil, liquid paraffin, paraffin oil and Purcellin oil.

The waxes are chosen from animal, fossil, vegetable, mineral or synthetic waxes. Special mention may be made of beeswax, carnauba, candellila, sugarcane and Japan waxes, ozokerites, montan wax, microcrystalline waxes and paraffins.

The compositions according to the invention can also contain, in addition to the indoline-based products as defined above, pigments which are generally used in cosmetics, in particular nacreous and/or pearlescent pigments which make it possible to vary the colorations capable of being obtained or to increase the protection with respect to ultraviolet radiation. In the latter case, pigments or nanopigments of metal oxides such as titanium, zinc, cerium or zirconium oxides are used more especially.

The nanopigments which are used preferentially are pigments having an average diameter of less than 100 nm and preferably of between 5 and 50 nm. They may be coated or uncoated.

The coated pigments are pigments which have undergone one or more surface treatments of a chemical, electronic, mecanochemical and/or mechanical nature with compounds such as those described, for example, in COSMETICS and TOILETRIES, February 1990, Vol. 105, pages 53–64, such as amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones, proteins (collagen, elastin), alkanolamines, silicon oxides, metal oxides or sodium hexametaphosphate.

When they are used for the temporary dyeing of hair, they take the form of more or less thickened lotions, of gel, of foam or of spray, containing the indoline-based product in an aqueous or water/solvent(s) medium in the proportions stated above.

When they are used for treatment of the nails, the indoline-based product is introduced into a nail-varnish medium comprising a volatile solvent and polymers.

Another subject of the invention consists of the process for the temporary dyeing of hair, making up the skin and the exoskeleton and protection of the human epidermis against the deleterious effects of UV radiation, employing the indoline-based products according to the invention.

These products may be applied directly in powder form or by means of cosmetic compositions as defined above.

The examples which follow are intended to illustrate the invention, no limitation, however, being implied thereby.

PREPARATION EXAMPLES

EXAMPLE 1

72.9 g (0.314 mol) of 5,6-dihydroxyindoline hydrobromide are solubilized in 500 ml of 0.1% aqueous ammonia solution. This solution is brought to 80° C. and an aqueous solution of sodium hydroxide containing 12.56 g (0.314 mol) of sodium hydroxide is added. 288 g of hydrogen peroxide solution containing 22.95 g (0.675 mol) of hydrogen peroxide are added to this mixture while the temperature is maintained at between 80° and 85° C. When the addition is complete, the temperature is maintained at 80° C. for 2 hours and the reaction medium is then cooled. The product is drained and washed with water. After drying, 38.5 g of black powder are obtained. This black powder can then be micronized according to conventional micronization processes.

In a variant of this process, the product before drying is transferred in a wet medium to a ball mill.

EXAMPLE 2

43.8 g (0.188 mol) of 5,6-dihydroxyindoline hydrobromide and 21.9 g (0.147 mol) of 5,6-dihydroxyindole are solubilized in 500 ml of 0.1% aqueous ammonia solution. This mixture is brought to 80° C. and an aqueous solution of sodium hydroxide containing 7.52 g (0.188 mol) of sodium hydroxide is added. 337.5 g of hydrogen peroxide solution containing 25.5 g (0.75 mol) of hydrogen peroxide are added to this mixture in the course of 2 h 30 minutes while the temperature is maintained at between 80° and 85° C. When the addition is complete, the temperature is maintained at 80° C. for 3 hours and the reaction medium is then cooled. The black product is drained and washed with water. After drying, 44.2 g of black powder are obtained, which powder can, as in Example 1, be micronized. The black product obtained before drying can, as in Example 1, be transferred in a wet medium to a ball mill.

EXAMPLE 3

0.12 g of mushroom tyrosinase is dissolved in 600 ml of 0.2M phosphate buffer whose pH is 6.8 g. 1.39 g (0.006 mol) of 5,6-dihydroxyindoline hydrobromide are added with stirring. Stirring is maintained for 4 hours in an atmosphere enriched with oxygen at a temperature between 35° C. and 37° C. The reaction medium is acidified to pH 3 with acetic acid. The precipitated product is centrifuged, washed with 250 ml of 0.1% acetic acid solution and then washed with water. After lyophilization, 0.93 g of black powder is obtained.

EXAMPLE 4

0.2 g of horseradish peroxidase, sold by the Company SIGMA, is dissolved in 4 liters of 0.2M acetate buffer whose pH is 4.5. 1 g ($4.3 \times 10^{-3}$ mol) of 5,6-dihydroxyindoline hydrobromide is added with stirring. 8 ml of hydrogen peroxide solution containing 2.6 g (0.078 mol) of hydrogen peroxide are then added. Stirring is maintained for 4 hours at a temperature of between 35° C. and 37° C. The product is isolated by centrifugation and then washed with water. After lyophilization, 0.62 g of black powder is obtained.

FORMULATION EXAMPLES

EXAMPLE 1

An anhydrous mascara of the following composition is prepared:
Carnauba wax 5.0 g
Candellila [sic] wax 5.0 g
Ethanol 3.0 g
Montmorillonite modified with an organic substance 4.0 g
Lanoline 2.0 g
Talc 10.0 g
Black powder of Example 1 2.0 g
Isoparaffin qs 100 g
This waterproof mascara is black.

EXAMPLE 2

An anhydrous mascara of the following composition is prepared:
Carnauba wax 5.0 g
Candellila wax 5.0 g
Ethanol 3.0 g
Montmorillonite modified with an organic substance 4.0 g
Lanolin 2.0 g
Talc 10.0 g
Black powder of Example 2 2.0 g
Isoparaffin qs 100 g
This waterproof mascara is black.
The procedure is as follows:
The waxes are heated to 80° C. The talc and pigments are added. The montmorillonite which has been modified with an organic substance and a part of the isoparaffin are then incorporated. At approximately 40° C., the ethyl alcohol and the remainder of the isoparaffin are introduced. The mixture is transferred to a grinder.

The mascara of Example 1 is also prepared according to this procedure.

We claim:
1. An indoline-based product having an average particle size of less than 50 microns, consisting essentially of the oxidative polymerization product resulting from the oxidative polymerization of one or more compounds wherein at least one of the one or more compounds is a compound of formula (I):

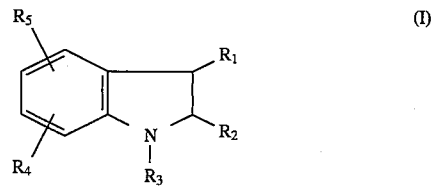

in which:
$R_1$ and $R_3$ represent, independently of one another, a hydrogen atom or a $C_1$–$C_4$ alkyl group;
$R_2$ represents a hydrogen atom, a $C_1$–$C_4$ alkyl group or a carboxyl or ($C_1$–$C_4$ alkoxy)carbonyl group;
$R_4$ denotes a hydrogen atom or a $C_1$–$C_4$ alkyl, hydroxyl, ($C_1$–$C_4$ alkoxy), amino or $C_1$–$C_{10}$ alkylamino or halogen group;
$R_5$ denotes a hydrogen atom or a hydroxy, $C_1$–$C_4$ alkoxy or amino group;

on condition that at least one of the radicals $R_4$ or $R_5$ denotes a hydroxyl, alkoxy or amino group; and with the proviso that when $R_5$ denotes an amino group, $R_4$ cannot denote an alkylamino radical;

$R_4$ or $R_5$ can also form a $C_1-C_2$ alkylenedioxy ring, and are at positions 5 and 6;

as well as the corresponding salts.

2. Product according to claim 1 wherein the compound of formula (I) is selected from the group consisting of 5,6-dihydroxyindoline, 6-hydroxyindoline, 5,6-methylenedioxyindoline, 7-methoxy-6-hydroxyindoline, 6,7-dihydroxyindoline, 5-hydroxy-4-methoxyindoline, 4,5-dihydroxyindoline, 5-methoxy-6-hydroxyindoline, 4-hydroxy-5-methoxyindoline, 5-hydroxy-6-methoxyindoline, 4,7-dihydroxyindoline, 6-aminoindoline, N-ethyl-4-hydroxyindoline, 1-ethyl-6-aminoindoline, 5,6-diaminoindoline, 1-methyl-6-aminoindoline, 2-methyl-6-aminoindoline, 3-methyl-6-aminoindoline, 2-methyl-5,6-diaminoindoline, 5-chloro-7-aminoindoline, 3-methyl-5,7-diaminoindoline, 5,7-diaminoindoline, 2-methyl-5,7-diaminoindoline, 7-aminoindoline, 2-methyl-7-aminoindoline, 4-aminoindoline, 4-amino-6-chloroindoline, 4-amino-6-iodoindoline, 4-amino-5-bromoindoline, 4-amino-5-hydroxyindoline, 4-amino-7-hydroxyindoline, 4-amino-5-methoxyindoline, 4-amino-7-methoxyindoline, 5-aminoindoline, 2,3-dimethyl-5-aminoindoline, 1-methyl-5-aminoindoline, 2-methyl-5-aminoindoline, 5-[N-(1-methylhexyl)amino]indoline, 5,6-dimethoxyindoline and 5,6-dihydroxy-2-carboxyindoline.

3. Product according to claim 1, wherein the product is the cooxidation product of at least one compound corresponding to the formula (I) and an indole derivative which is a mono- or dihydroxyindole or aminoindole.

4. Product according to claim 3, wherein the indole derivative corresponds to the formula:

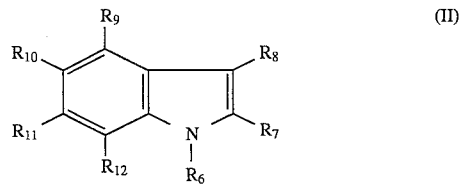

in which:

$R_6$ and $R_8$ denote, independently of one another, a hydrogen atom or a $C_1-C_4$ alkyl group;

$R_7$ represents a hydrogen atom, a $C_1-C_4$ alkyl group, a carboxyl group or a ($C_1-C_4$ alkoxy)carbonyl group;

$R_9$ and $R_{12}$ denote, independently of one another, a hydrogen atom, a hydroxyl group or a $C_1-C_4$ alkyl, amino, ($C_1-C_4$ alkoxy), ($C_2-C_4$ acyl)oxy or ($C_2-C_4$ acyl)amino group;

$R_{10}$ denotes hydrogen or a hydroxyl, ($C_1-C_4$ alkoxy), ($C_1-C_4$ alkyl), halogen, amino, ($C_2-C_{14}$ acyl)oxy, ($C_2-C_4$ acyl)amino or trimethylsilyloxy group;

$R_{11}$ denotes hydrogen or a hydroxyl, ($C_1-C_4$ alkoxy), amino, ($C_2-C_4$ acyl)oxy, ($C_2-C_4$ acyl)amino, trimethylsilyloxy or hydroxy($C_2-C_4$ alkyl)amino group;

$R_{10}$ and $R_{11}$, together with the carbon atoms to which they are attached, can form a methylenedioxy ring optionally substituted with a $C_1-C_4$ alkyl or $C_1-C_4$ alkoxy group or a carbonyldioxy ring;

at least one of the groups $R_9$ to $R_{12}$ represents a group OZ or NHR, not more than one of the groups $R_9$ to $R_{12}$ denoting NHR;

and not more than two of the groups $R_9$ to $R_{12}$ denote OZ, in the case where Z denotes hydrogen, these groups are at positions 5 and 6;

and at least one of the groups $R_9$ to $R_{12}$ represents hydrogen, in the case where only one of these groups denotes hydrogen, only one group from among $R_9$ to $R_{12}$ then denotes NHR or OZ and the other groups denote $C_1-C_4$ alkyl; R in NHR denoting a hydrogen atom or a $C_2-C_4$ acyl or $C_2-C_4$ hydroxyalkyl group, and Z in OZ denoting a hydrogen atom or a $C_2-C_{14}$ acyl, $C_1-C_4$ alkyl or trimethylsilyl group;

and the corresponding salts.

5. Product according to claim 4, wherein the product is prepared by cooxidation of an indoline derivative of formula (I) and an indole derivative of formula (II), up to 50 mol % of indole derivative of formula (II) being used relative to the total number of moles of compounds to be oxidized.

6. Process for preparing the product according to claim 1, wherein the oxidation is performed in the presence of an oxidizing agent which is sodium nitrite, ortho- or para-benzoquinone monoimines or diimines, 1,2- or 1,4-naphthoquinones or 1,2- or 1,4-naphthoquinone mono- or diimines.

7. Process for preparing the products according to claim 1, wherein the oxidation is performed enzymatically and the colored indoline based product thereby formed is isolated by filtration, centrifugation or lyophilization.

8. Process for preparing the products according to claim 4, wherein the cooxidation is performed by introduction, in aqueous solution in a water/solvent or anhydrous medium in a first stage, of the compound of formula (I) with indoles of formula (II), and, in a second stage, of an oxidizing agent in sufficient amounts to form the indoline-based product and wherein the indoline based product thereby formed is isolated by filtration, centrifugation or lyophilization.

9. Process according to claim 8, wherein the solvent is selected from the group consisting of $C_1-C_4$ lower alcohols, alkylene glycols, alkylene glycol alkyl ethers and methyl lactate.

10. Process according to claim 8, wherein the compound of formula (I) and the indoles of formula (II) represent from 0.1 to 30% by weight relative to the weight of the reaction medium.

11. Cosmetic composition, comprising 0.1 to 35% by weight, in a cosmetically acceptable medium, of a product as defined in claim 1.

12. Composition according to claim 11, in the form of a lotion, thickened lotion, gel, cream, milk, powder or stick, optionally packaged as an aerosol in the form of a spray or foam.

13. Composition according to claim 11, for use on the skin, nails, eyelashes, eyebrows or in anhydrous or aqueous pasty, solid or liquid form.

14. Composition according to claim 11, wherein the composition is intended for protection of the human epidermis against UV radiation, and is in the form of a suspension or dispersion in solvents or fats or the form of an emulsion, pomade, gel, solid stick or aerosol foam.

15. Composition according to claim 11, wherein it contains fats, organic solvents, silicones, thickeners, demulcents, surfactants, sunscreen agents, antifoams, hydrating agents, perfumes, preservatives, antioxidants, fillers, sequestering agents, treatment agents, propellants, alkalinizing or acidifying agents or other pigments.

16. Process for the temporary dyeing of hair, comprising applying a composition as defined in claim 11 to the hair.

17. Process for cosmetically treating the skin or the exoskeleton, comprising applying a composition according to claim 11 to the skin or the exoskeleton.

* * * * *